United States Patent [19]

Rath et al.

[11] Patent Number: 5,278,189
[45] Date of Patent: Jan. 11, 1994

[54] PREVENTION AND TREATMENT OF OCCLUSIVE CARDIOVASCULAR DISEASE WITH ASCORBATE AND SUBSTANCES THAT INHIBIT THE BINDING OF LIPOPROTEIN (A)

[76] Inventors: Matthias W. Rath, Eberhardstrasse 12, 7141 Kirchberg/Murr, Fed. Rep. of Germany; Linus C. Pauling, 15 Salmon Creek, Big Sur, Calif. 93920

[21] Appl. No.: 557,516

[22] Filed: Jul. 24, 1990

Related U.S. Application Data

[63] Continuation-in-part of Ser. No. 533,129, Jun. 4, 1990, abandoned.

[51] Int. Cl.$^5$ .................. A61K 31/195; A61K 31/34; A61K 31/44
[52] U.S. Cl. .............................. 514/561; 514/356; 514/474; 514/824
[58] Field of Search .............. 514/474, 561, 562, 564, 514/567, 824, 356

[56] References Cited

U.S. PATENT DOCUMENTS

| | | | |
|---|---|---|---|
| 3,956,504 | 5/1976 | Sawyer | 514/567 |
| 4,424,232 | 1/1984 | Parkinson | 514/474 |
| 4,600,582 | 7/1986 | Stevens et al. | 514/561 |
| 4,954,521 | 9/1990 | Sawyer et al. | 514/474 |

FOREIGN PATENT DOCUMENTS

| | | |
|---|---|---|
| 60-4611 | of 1985 | Japan . |
| 60-78560 | of 1985 | Japan . |
| 60-87221 | of 1985 | Japan . |

OTHER PUBLICATIONS

Chemical Abstracts 77(13):86318 (1972).
*Vitamin C in Health and Disease*, Basu et al., AVI Publishing Co., Inc. (1982) pp. 95-101.
*Martindale, The Extra Pharmacopoeia*, 28th edition (1982) p. 56, "Lysine Hydrochloride".
*The Nutrition Desk Reference*, Garrison et al, Keats Publishing Inc. (1985) pp. 172-177.
Rath, M. & L. Pauling, "Solution of the puzzle of human cardiovascular disease: Its primary cause is ascorbate deficinecy leading to the deposition of lipoprotein(a) and fibrinogen/fibrin in the vascular wall," J. Orthomolecular Med. (In Press 1991).
Markwardt, F. & H. P. Klocking, "Chemical control of hyperfibrinolytic states by synthetic inhibitors of fibrinolytic enzymes," Biomed. Biochim. Acta 42:725-730 (1983).
Werb, Z. et al., "Endogenous activation of latent collagenase by rheumatoid synovial cells," New England J. Med. 296(18):1017-1023 (1977).
Knox, E. G., "Ischaemic-heart-disease mortality and dietary intake of calcium," Lancet, i, pp. 1465-1467, Jun. 30, 1973.
Berg, K. "A new serum type system in man—The LP system," Acta Path. 59:369-382 (1963).
McLean, J. et al., "cDNA sequence of human apolipoprotein(a) is homologous to plasminogen," Nature 300:132-137 (1987).
Salonen, E-M, et al., "Lipoprotein(a) binds to fibronectin and has serine proteinase activity capable of cleaving it," EMBO J. 8(13):4035-4040 (1989.
Harpel, P.C. et al., "Plasmin catalyzes binding of lipoprotein(a) to immobilized fibrinogen and fibrin," Proc. Natl. Acad. Sci. USA 86:3847-3851 (1989).
Gonzalez-Gronow, M. et al., "Further characterization of the cellular plasminogen biding site: Evidence that Plasminogen 2 and Lipoprotein a compete for the same site," Biochemistry 28:2374-2377 (1989).
Hajjar, K. A. et al., "Lipoprotein(a) modulation of endothelial cell surface fibrinolysis and its potential role in atherosclerosis," Nature 339:303-305 (1989).

(List continued on next page.)

*Primary Examiner*—Frederick E. Waddell
*Assistant Examiner*—Raymond J. Henley, III
*Attorney, Agent, or Firm*—Limbach & Limbach

[57] ABSTRACT

A method is provided for prevention and treatment of cardiovascular disease, such as atherosclerosis, by administering therapeutically effective dosages of a drug comprised of ascorbate, lipoprotein(a) binding inhibitors, and antioxidants.

15 Claims, 5 Drawing Sheets

OTHER PUBLICATIONS

Armstrong, V. W. et al., "The association between serum Lp(a) concentrations and angiographically assessed coronary atherosclerosis"; Atheroscloerosis 62:249–257 (1986).

Dahlen, G. H. et al., "Association of levels of lipoprotein Lp(a), plasma lipids, and other lipoproteins with coronary artery disease documented by angiography," Circulation 74(4): 758–765 (1986).

Miles, L. A. et al., "A potential basis for the thrombotic risks associated with Lipoprotein (a)," Nature 339:301–302 (1989).

Zenker, G. et al., "Lipoprotein(a) as a strong indicator for cerebrovascular disease," Stroke 17(5)942–945 (1986).

Zechner, R. et al., "Fluctuations of plasma Lipoprotein-A concentrations during pregnancy and post partum," Metabolism 35(4):333–336 (1986).

Hoff, H. et al., "Serum Lp(a) level as a predictor of vein graft stenosis after coronary artery bypass surgery in patients," Circulation 77(6):1238–1244 (1988).

Rath, M. et al., "Detection and quantification of Lipoprotein(a) in the arterial wall of 107 coronary bypass patients," Arteriosclerosis 9(5):579–592 (1989).

Cushing, G. L. et al., "Quantitation and localization of Apolipoproteins [a] and B in Coronary artery bypass vein grafts resected at re-operation," Arteriosclerosis 9(5):593–603 (1989).

Bruckert, E. et al., "Increased serum levels of Lipoprotein(a) in diabetes mellitus and their reduction with glycemic control," JAMA 263(1):35–36 (1990).

Blumberg, B., et al., "A human lipoprotein polymorphism," J. Clin. Invest. 41:1936–1944 (1962).

Eaton, D. L., et al., "Partial amoni acid sequence of apolipoprotein(a) shows that it is homologous to plasminogen," Proc. Natl. Acad. Sci. USA, 84:3224–3228 (1987).

Wright, L. C. et al., "Elevated apolipoprotein(a) levels in cancer patients," Int. J. Cancer 43:241–244 (1989).

Som, S. et al., "Ascorbic acid metabolism in diabetes mellitus," Metabolism 30:572–577 (1981).

Maeda, S. et al., "Transient changes in serum lipoprotein(a) as an acute phase protein," Atherosclerosis 78:145–150 (1989).

Kapeghian, J. C. et al., "The effects of glucose on ascorbic acid uptake in heart, endothelial cells: Possible pathogenesis of diabetic angiopathies," Life Sci. 34:577 (1984).

Tomlinson, J. E. et al., "Rhesus monkey apolipoprotein(a)," J. Biol. Chem. 264:5957–5965 (1989).

Ginter, E. et al., "The effect of chronic hypovitaminosis C on the metabolism of cholesterol and athergenesis in guinea pigs," J. Atherosclerosis Res. 10:341–352 (1969).

PREVENTION AND TREATMENT OF OCCLUSIVE CARDIOVASCULAR DISEASE WITH ASCORBATE AND SUBSTANCES THAT INHIBIT THE BINDING OF LIPOPROTEIN (A)

This application is a continuation-in-part of application Ser. No. 07/533,129, filed Jun. 4, 1990.

TECHNICAL FIELD

The present invention relates generally to the prevention and treatment of cardiovascular disease and more particularly to methods and compounds that inhibit the binding of lipoprotein (a) to components of the arterial wall.

BACKGROUND OF THE INVENTION

Lipoprotein(a) ("Lp(a)") was first identified by Blumberg, B. S., et al. (1962) J. Clin. Invest. 41: 1936–1944, and Berg, K. (1963) Acta Pathol. 59: 369–382. The structure of Lp(a) resembles that of low-density lipoprotein ("LDL") in that both share a lipid apoprotein composition, mainly apolipoprotein B-100 ("apo B"), the ligand by which LDL binds to the LDL receptors present on the interior surfaces of arterial walls. The unique feature of Lp(a) is an additional glycoprotein, designated apoprotein(a), apo(a), which is linked to apo B by disulfide groups. The cDNA sequence of apo(a) shows a striking homology to plasminogen, with multiple repeats of kringle 4, one kringle 5, and a protease domain. The isoforms of apo(a) vary in the range of 300 to 800 kDa and differ mainly in their genetically determined number of kringle 4 structures. McLean, J. W., et al. (1987) Nature 300: 132–137. Apo(a) has no plasmin-like protease activity. Eaton, D. L., et al., (1987) Proc. Natl Acad. Sci. USA, 84: 3224–3228. Serine protease activity, however, has been demonstrated. Salonen, E., et al. (1989) EMBO J. 8: 4035–4040. Like plasminogen, Lp(a) has been shown to bind to lysine-sepharose, immobilized fibrin and fibrinogen, and the plasminogen receptor on endothelial cells. Harpel, P.C., et al. (1989) Proc. Natl. Acad. Sci. USA 86:3847–3851; Gonzalez-Gronow, M., et al. (1989) Biochemistry 28: 2374–2377; Miles, L. et al. (1989) Nature 339: 301–302; Hajjar, K. A., et al. (1989) Nature 339: 303–305. Furthermore, Lp(a) has been demonstrated to bind to other components of the arterial wall like fibronectin and glycosaminoglycans. The nature of these bindings, however, is poorly understood.

Essentially all human blood contains lipoprotein(a); however, there can a thousand-fold range in its plasma concentration between individuals. High levels of Lp(a) are associated with a high incidence of cardiovascular disease. Armstrong, V. W., et al. (1986) Atherosclerosis 62: 249–257; Dahlen, G., et al. (1986) Circulation 74: 758–765; Miles, L. A., et al. (1989) Nature 339: 301–302; Zenker, G., et al. (1986). Stroke 17: 942–945 (The term occlusive cardiovascular disease will be used hereafter as including all pathological states leading to a narrowing and/or occlusion of blood vessels throughout the body, but particularly atherosclerosis, thrombosis and other related pathological states, especially as occurs in the arteries of the heart muscle and the brain.)

For some time, general medical practice has focused on the role of LDL, the so called "bad cholesterol," in occlusive cardiovascular disease. A great many studies have been published ostensibly linking occlusive cardiovascular disease with elevated levels of LDL. As a result, most therapies for the treatment and prevention of arteriosclerosis rely on drugs and methods for the reduction of serum levels of LDL's. Such therapies have had mixed results. The efficacy of such approaches to the problem of occlusive cardiovascular disease continues to be major source of debate.

There exists therefore a need for a drug therapy for reducing the binding of Lp(a) to vessel walls, for reducing the overall level of Lp(a) in the circulatory system and for promoting the release of existing deposits of Lp(a) on vessel walls.

SUMMARY OF THE INVENTION

The foregoing needs in the treatment and prevention of cardiovascular disease are met by the methods and compositions of the present invention.

A method is provided for the treatment of occlusive cardiovascular disease, comprising the step of administering to a subject an effective amount of ascorbate and one or more binding inhibitors, as a mixture or as a compound comprising ascorbate covalently linked with binding inhibitors, which inhibit the binding of Lp(a) to blood vessel walls, such as arterial walls. This effect may also be obtained by administering an effective amount of one or more inhibitors, without ascorbate. The term binding inhibitor throughout the specification and claims is intended to include all substances that have an affinity for the lysine binding site present on the interior walls of blood vessels, particularly arteries, the site of Lp(a) binding. Most of these substances compete with plasmin for the lysine binding site and some of these compounds, in high doses, are in clinical use for the treatment of hyperfibrinolytic states.

A method is further provided for the prevention of atherosclerosis comprising the step of administering to a subject an effective amount of ascorbate and one or more binding inhibitors as previously discussed but further comprising one or more antioxidants. The term antioxidant throughout the specification and the claims is intended to exclude ascorbate which has as one of its chemical properties a potent antioxidant effect.

It is thus an object of the invention to provide a method for treatment of occlusive cardiovascular disease by administering to a subject an effective amount of ascorbate and one or more binding inhibitors, or an effective amount of one or a mixture of binding inhibitors.

It is another object of the invention to provide a method for preventing of occlusive cardiovascular disease, by administering to a subject an amount of ascorbate effective to lower the amount of Lp(a) in the plasma of the subject.

Yet another object of the present invention is to provide a method for prevention of cardiovascular disease by administering to a subject an effective amount of ascorbate and one or more binding inhibitors, or an effective amount of one or more binding inhibitors.

A further object of the present invention is to provide a pharmaceutically acceptable agent for the treatment of occlusive cardiovascular disease.

Still another object of the present invention is to provide a pharmaceutically acceptable agent for the prevention of cardiovascular disease.

These and other objects will be more readily understood upon consideration of the following detailed descriptions of embodiments of the invention and the drawings.

DETAILED DESCRIPTION OF THE INVENTION

Figure 1:
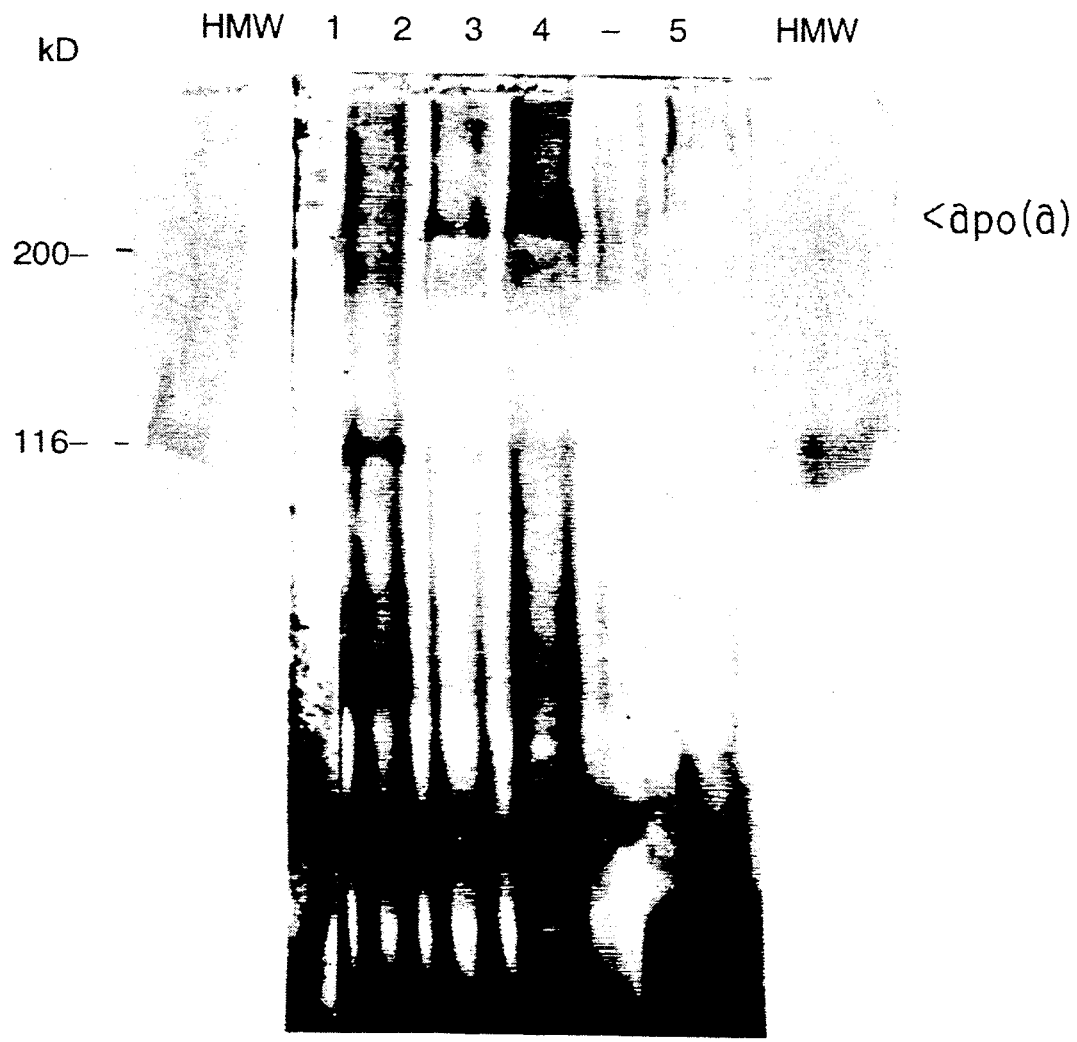
FIG. 1 is an immunoblot of the plasma of guinea pigs form from the test described in Example 1.

Our invention is based in part on our discovery that animals which have lost the ability to produce ascorbate, such as higher primates and guinea pigs, uniformly produce Lp(a). Most animals which possess the ability to synthesize ascorbate generally do not produce Lp(a). Further, we have found that ascorbate deficiency in humans and guinea pigs tends to raise Lp(a) levels and causes atherosclerosis by the deposition of Lp(a) in the arterial wall, from which we conclude that ascorbate administration lowers plasma Lp(a) levels.

We have also discovered that substances that inhibit the binding of Lp(a) to components of the arterial wall, particularly to fibrinogen, fibrin and fibrin degradation products herein identified as binding inhibitors, such as lysine or ε-aminocaproic acid used alone or in combination with ascorbate, cause release of Lp(a) from the arterial wall. Thus, ascorbate and such binding inhibitors are not only useful for the prevention of occlusive cardiovascular disease, but also for the treatment of such disease. The present invention, then, provides methods and pharmaceutical agents for the both the treatment and prevention of occlusive cardiovascular disease in vivo.

GENERAL APPLICATIONS

The present invention provides a method and pharmaceutical agent for the treatment and prevention of occlusive cardiovascular disease generally, by administering to a subject an effective amount of ascorbate and one or more binding inhibitors. Throughout the specification and claims, the term binding inhibitor is intended to cover any substance which has as at least one of its chemical properties the ability to inhibit the binding of Lp(a) to blood vessel wall components, particularly to fibrin or fibrinogen. As used herein, the term "ascorbate" includes any pharmaceutically acceptable salt of ascorbate, including sodium ascorbate, as well as ascorbic acid itself. Binding inhibitors include, but are not limited to ε-aminocaproic acid, lysine, tranexamic acid (4-aminomethylcyclohexane carboxylic acid), p-aminomethylbenzoic acid, p-benzylamine sulfuric acid, o-N-acetyl-lysine-methyl ester, PROBUCOL (a compound comprised of 2 butyl hydroxy tocopherol groups linked together by a disulphide group), Aprotinin, trans-4-aminomethylcyclohexanecarboxylic acid (AMCA), and benzamidine derivatives such as amidinophenylpyruvic acid (APPA) and 1-naphthyl-(1)-3-(6-amidinonaphthyl-(2))-propanone-1 HCl (NANP). An effective amount of a binding inhibitor or a mixture of binding inhibitors may also be used, without ascorbate. Other substances used in the treatment of occlusive cardiovascular disease may be co-administered, including antioxidants, such as tocopherol, carotene and related substances; vitamins; provitamins; trace elements; lipid-lowering drugs, such as hydroxy-methyl-glutaryl coenzyme A reductase inhibitors, nicotinic acid, fibrates, bile acid sequestrants; and mixtures of any two or more of these substances.

Although ascorbate can be used alone or in varying combinations with one or more representative constituents of the above classes of compounds, we prefer when treating a pre-existing cardiovascular condition to combine ascorbate with at least one each of the binding inhibitors, antioxidants and lipid lowering drugs elements in the dosages (per kilogram of body weight per day (Kg BW/d)) provided in Table 1. It should be noted that Table 1 provides differing concentration ranges of each constituent, depending upon whether the agent is to be administered orally or parenterally. The variance in dosages is reflective of variation in disease severity. It will be realized therefore that if the subject has been diagnosed for advanced stages of atherosclerosis, dosages at the higher end of this range can be utilized. However, if only prevention of an atherosclerosis condition is the object, dosages at the lower end of this range can be utilized.

As an alternative, a pharmaceutical agent identical to the one just described, but omitting ascorbate, may be employed.

Where ascorbate and binding inhibitors are utilized in the same agent, they may simply be mixed or may be chemically combined using synthesis methods well known in the art, such as compounds in which ascorbate and the inhibitor are covalently linked, or form ionically bound salts. For example, ascorbate may be bound covalently to lysine, other amino acids, or ε-aminocaproic acid by ester linkages. Ascorbyl ε-aminocaproate is such an example. In this form the ascorbate moiety may be particularly effective in preventing undesirable lipid peroxidation.

In the case of oral administration, a pharmaceutically acceptable and otherwise inert carrier may be employed. Thus, when administered orally, the active ingredients may be administered in tablet form. The tablet may contain a binder such as tragacanth, corn starch or gelatin; a disintegrating agent, such as alginic acid, and/or a lubricant such as magnesium stearate. If administration in liquid form is desired, sweetening and/or flavoring agents may be used. If administration is by parenteral injection, in isotonic saline, a phosphate buffered solution or the like, may be used as a pharmaceutically acceptable carrier.

The advisability of using binding inhibitors in treating occlusive cardiovascular disease will depend to some extent on the subject's general health, particularly with regard to hyperfibrinolytic conditions. Most binding inhibitors (except lysine) are used clinically to treat such conditions. As a result, monitoring of the subject's coagulation and fibrinolytic sysem is recommended before and during treatment for occlusive cardiovascular disease. Long-term administration of binding inhibitors will require formulations in which the dosages of binding inhibitors are in the lower ranges of the dosages given in Table 1.

Prevention, as contrasted with treatment, of cardiovascular disease may be accomplished by oral or parenteral administration of ascorbate alone. Table 1 gives a range of ascorbate concentrations sufficient to lower the serum Lp(a) concentration.

Preferably the prevention of the occlusive cardiovascular disease according to the invention is accomplished by use of a physical mixture of ascorbate and one or more binding inhibitors, or by use of a compound comprising covalently linked ascorbate with one or more of the binding inhibitors, which inhibit binding of Lp(a) to the arterial wall. A binding inhibitor or mixture of binding inhibitors may also be administered without ascorbate to prevent Lp(a)-associated occlusive cardiovascular disease.

To optimize the therapeutic effect of the release of Lp(a) from the blood vessel walls, the ascorbate and the binding inhibitors described above may be separately administered. Further optimization of therapeutic effect can be gained by using a time release composition to achieve relatively constant serum concentrations of the agent through time.

TABLE 1
DOSAGES OF COMPONENTS IN THE DRUG COMPOSITIONS OF THE PRESENT INVENTION

|  | Oral Administration | Parenteral Administration |
|---|---|---|
| Ascorbate: | 5 mg–2500 mg/kg bw/d | 25 mg–2500 mg/kg bw/d |
| Binding inhibitors: |  |  |
| EACA | 5 mg–500 mg/kg bw/d | same |
| Tranexamic Acid | 1 mg–100 mg/kg bw/d | same |
| Para-aminomethyl benzoic acid | 1 mg–30 mg/kg bw/d | same |
| Lysine | 5–500 mg/kg bw/d | same |
| Antioxidants: |  |  |
| Tocopherol | 0,1 IU–20 IU/kg bw/d | same |
| Carotene | 100 IU–1000 IU/kg bw/d | same |
| Lipid Lowering Drugs: |  |  |
| Nicotinic Acid | 1 mg–300 mg/kg bw/d |  |
| HMG-CoA | 0.1–10 mg/kg bw/d |  |
| Fibrates | 0.1–20 mg/kg bw/d |  |
| Probucol | 0.1–20 mg/kg bw/d |  |
| Bile Acid Sequestrants | 10–400 mg/kg bw/d |  |

TABLE 2
CONCENTRATION OF COMPONENTS IN THE SOLUTION OF THE PRESENT INVENTION

| Ascorbate | 50–5000 mg/l |
|---|---|
| Binding inhibitors |  |
| EACA | 2–2000 mg/l |
| Tranexamic Acid | 1–300 mg/l |
| Para-aminomethyl benzoic acid | 1–200 mg/l |
| Lysine | 10–5000 mg/l |
| Antioxidants |  |
| Tocopherol | 1–1000 mg/l |
| Carotene | 0.1–100 mg/l |

EXPERIMENTAL

Having disclosed the preferred embodiment of the present invention, the following examples are provided by way of illustration only and are not intended to limit the invention in any way.

EXAMPLE 1

Because of its metabolic similarity to man, with resepct to the metabolism of ascorbate and Lp(a), the guinea pig was used in this example.

No study has been previously reported in the guinea pig to identify the lopoprotein involved as risk factors in plasma and as constituents of the atherosclerotic plaque.

Three female Gartly guinea pigs with an average weight of 800 g and an approximate age of 1 year wer stuided. One animal received an extreme hypoascorbic diet with 1 mg ascorbate/kg body weight/d. Another animal received 4 mg/kg BW/d. The third animal served as a control receiving 40 mg ascorbate/kg/BW/d)

Blood was drawn by heart puncture from the anesthetized animals and collected into EDTA containing tubes at the beginning, after 10 days, and after 3 weeks, when the animals were sacrificed. Plasma was stored at $-80°$ C. until analyzed. Lp(a) was detected in the plasma of the guinea pigs by use of SDS-polyacrylamide gels according to Neville (*J. Biol. Chem.*, 246, 6328–6334 (1971)) followed by Western blotting (Beisiegel, et al., *J. Biol. Chem.*, 257, 13150–13156 (1982)). 40 μl of plasma and 20 mg of arterial wall homogenate were applied in delipidated form per lane of the gel. The immunodetection of apo(a) was performed using a polyclonal anti-human apo(a) antibody (Immuno, Vienna, Austria) followed by a rabbit anti-sheep antibody (Sigma) and the gold-conjugated goat anti-rabbit antibody with subsequent silver enhancement (Bio-Rad). The determinations of cholesterol and triglycerides were done at California Veterinary Diagnostics (Sacramento) using the enzyme assay of Boehringer Mannheim. Plasma ascorbate was determined by the dinitrophenylhydrazine method (Schaffer, et al., *J. Biol. Chem.*, 212, 59 (1955)).

Figure 2:
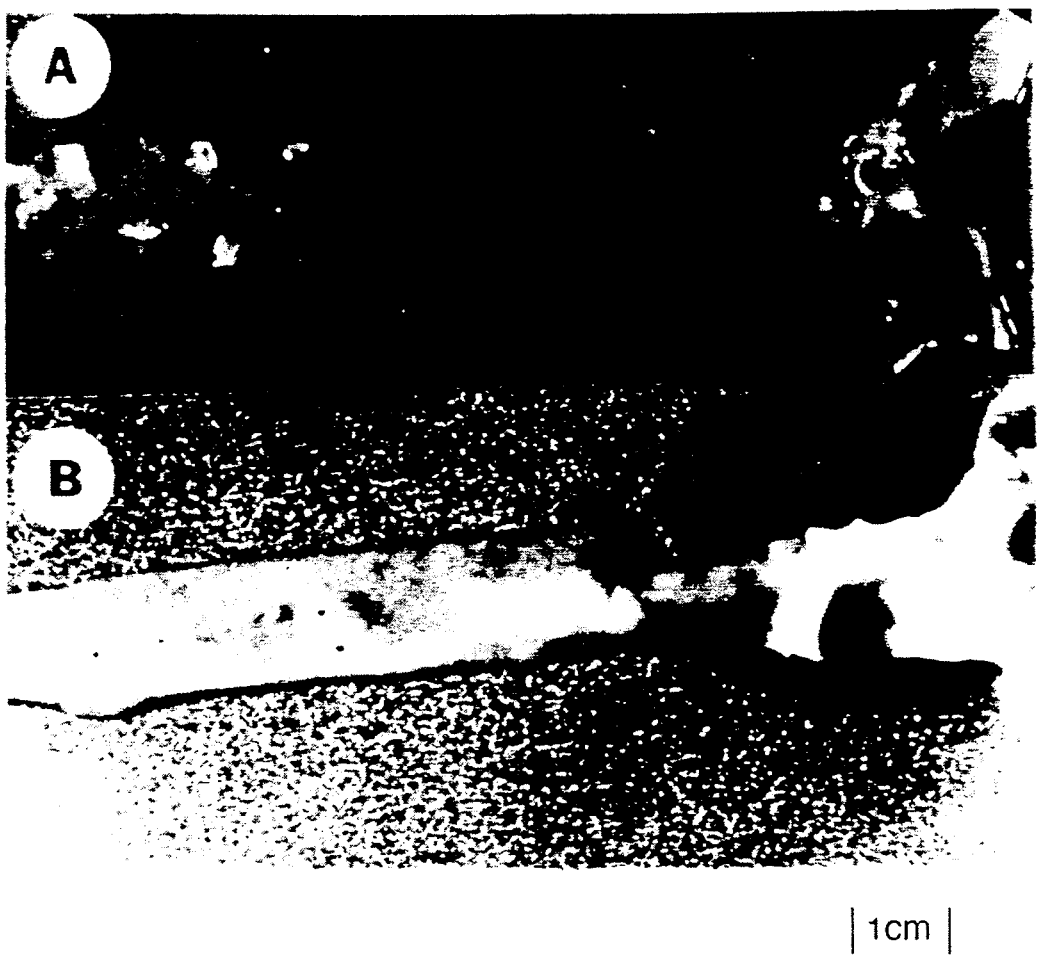
FIG. 2A a photograph of the aorta of a guinea pig receiving an adequate amount of ascorbate from the test diet in Example 1.
FIG. 2B is a photograph of an aorta of a guinea pig receiving a hypoascorbic diet after three weeks from the test diet in Example 1.
Figure 3:
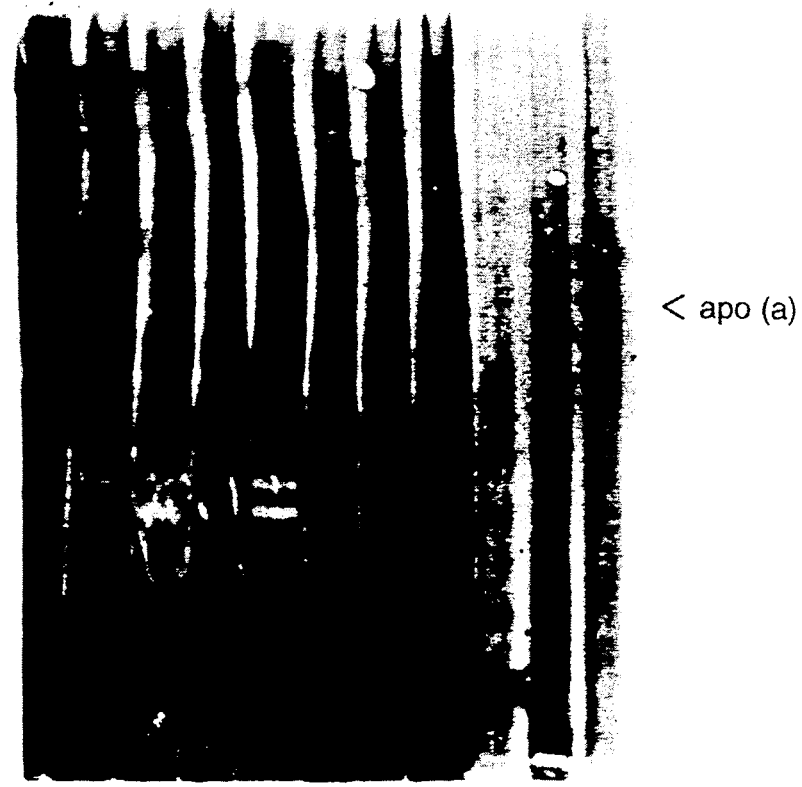
FIG. 3 is an immunoblot of plasma and tissue of guinea pigs from the test shown in Example 2.
Figure 5:
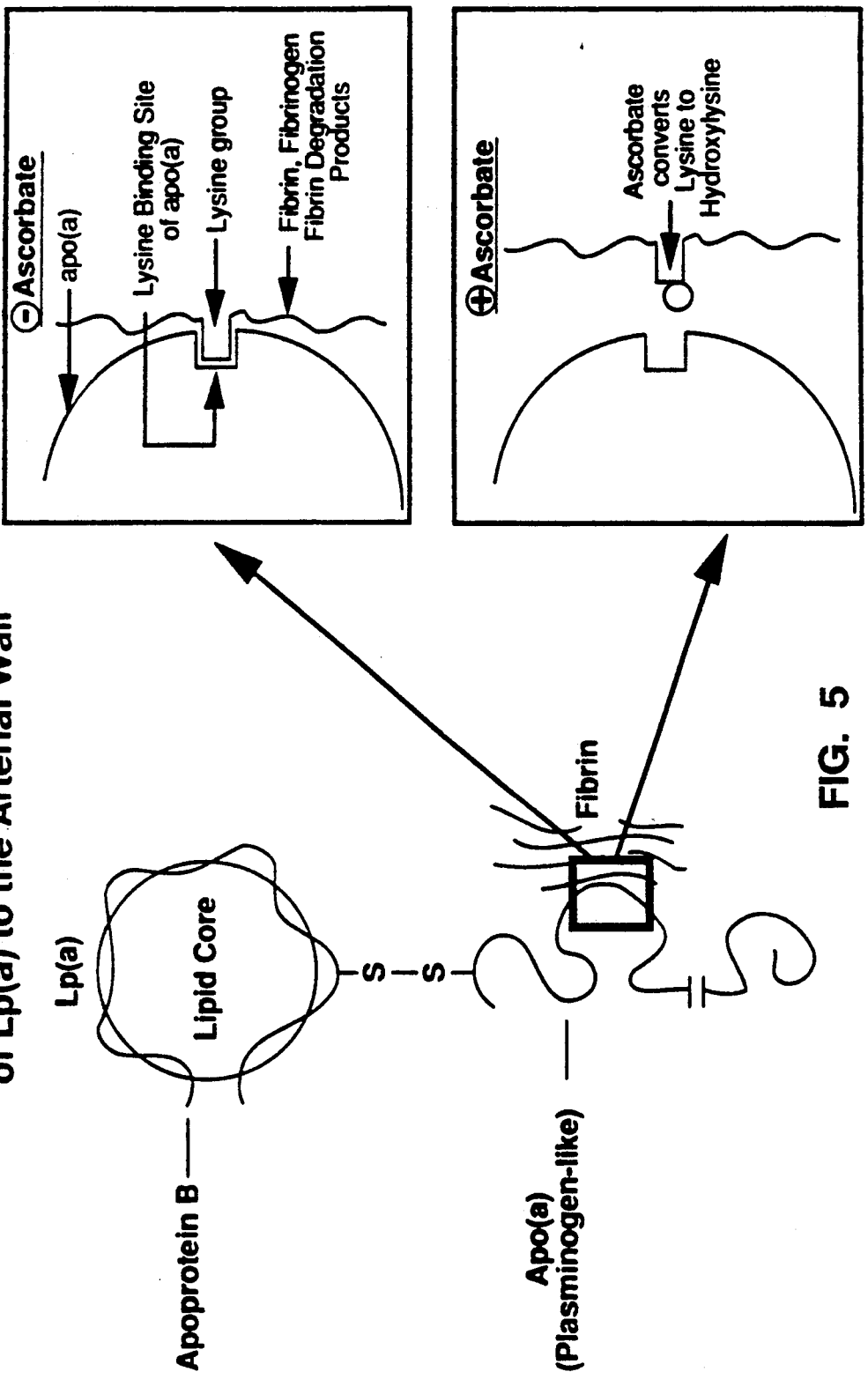
FIG. 5 show the potential mechanism of ascorbate in the binding of Lp(a) to the arterial wall.
Figure 4:
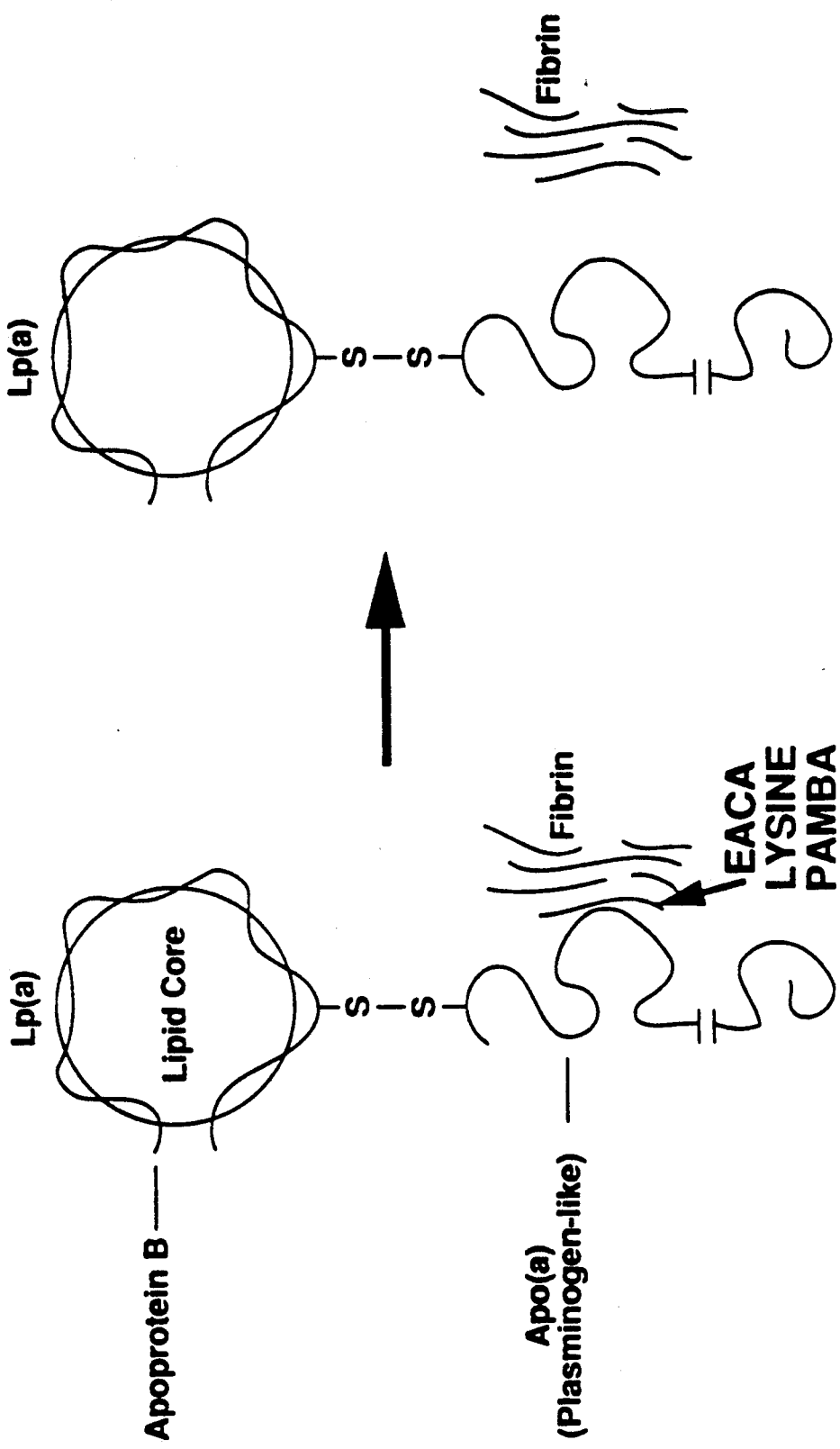
FIG. 4 shows the potential mechanism of binding inhibitors in the therapy for atherosclerosis.

Vitamin C deficiency in the diet led to an increase of Lp(a) in the plasma of the guinea pig indicated by a clear band in the immunoblot of the plasma after 10 and 20 days of a hypoascorbic diet (FIG. 1). At necropsy the animals were anesthetized with metophase and were exsanguinated. Aorta, heart and various other organs were taken for biochemical and histological analysis. The aorta was excised, the adventitial fat was carefully removed, and the vessel was opened longitudinally. Subsequently the aorta was placed on a dark metric paper and a color slide was taken. The picture was projected and thereby magnified by an approximate factor 10. The circumference of the ascending aorta, the aortic arch and thoracic aorta as well as the atherosclerotic lesions in this area were marked and measured with a digitalized planimetry system. The degree of atherosclerosis was expressed by the ratio of plaque area to the total aortic area defined. The difference in the 3 one-year old animals of the experiment was significant and pronounced lesions were observed in the ascending aorta and the arch of the vitamin C deficient animal (FIG. 2B).

EXAMPLE 2

To confirm the data obtained in Example 1, a second guinea pig experiment was conducted, using 33 male animals with a mean weight of 550 g and an approximate age of 5 months. One group of 8 animals served as a control and received 40 mg ascorbate/kg BW/d (group A). To induce hypoascorbemia 16 animals were fed 2 mg ascorbate/kd/d (group B). Group A and half of the animals of group B (progression sub-group) were sacrificed after 5 weeks as described above. Half of group B was kept for 2 more weeks, receiving daily intraperitoneal injection of 1.3 g sodium ascorbate/Kg BW/d as a daily intra peritoneal injection with the intention to reduce the extent of atherosclerosis lesions. After this period these animals also were sacrificed.

Plasma ascorbate levels were negatively correlated with the degree of the atherosclerotic lesion. Total cholesterol levels increased significantly during ascorbic acid deficiency (Table 3).

The aortas of the guinea pigs receiving a sufficient amount of ascorbate were essentially plaque free, with minimal thickening of the intima in the ascending region. In contrast, the ascorbate-deficient animals exhibited fatty streak-like lesions, covering most parts of the ascending aorta and the aortic arch. In most cases the branching regions of the intercostal arteries of the aorta exhibited similar lipid deposits. The difference in the precentage of lesion area between the control animals and the hypoascorbic diet animals was 25% deposition of lipids and liporpoteins in the arterial wall.

TABLE 3

MEAN PLASMA PARAMETERS OF THE DIFFERENT GROUPS IN RELATION TO THE AREA OF AORTIC LESIONS

|  | Control | Scurvy (progress) | Regression (after Scurvy) |
|---|---|---|---|
| Plasma Chloesterol (mg/dl) | 39 | 54 | 33 |
| Total Plasma Ascorbic Acid µg/ml | 5.03 | 3.01 | 20.64 |
| Atheroscl. Lesion (Percent of Aorta Thorac. Surface) | — | 25 | 19 |

EXAMPLE 3

Human arterial wall was obtained post mortem from the aorta ascendens. The tissue showed homogeneous intimal thickening (early atherosclerotic lesion). It was cut into pieces, with 100 mg of the cut up tissue homogenized in a glass potter for a 1 minute in 2.5 ml of the following solutions:

| | |
|---|---|
| PBS (Dulbeco) + NaAscorbate | 50 mg/ml |
| PBS + EACS | 50 mg/ml |
| PBS + Tranexamic Acid | 50 mg/ml |
| PBS + NaAscorbate + Tranexamic Acid | 50 mg/ml |

Results of this treatment are given in Table 4 and show that, compared to the control solution, a considerable amount of Lp(a) was released from the interior arterial wall.

TABLE 4

Lp(a) RELEASED FROM HUMAN AORTA IN RELATION TO SPECIFIC BINDING INHIBITORS

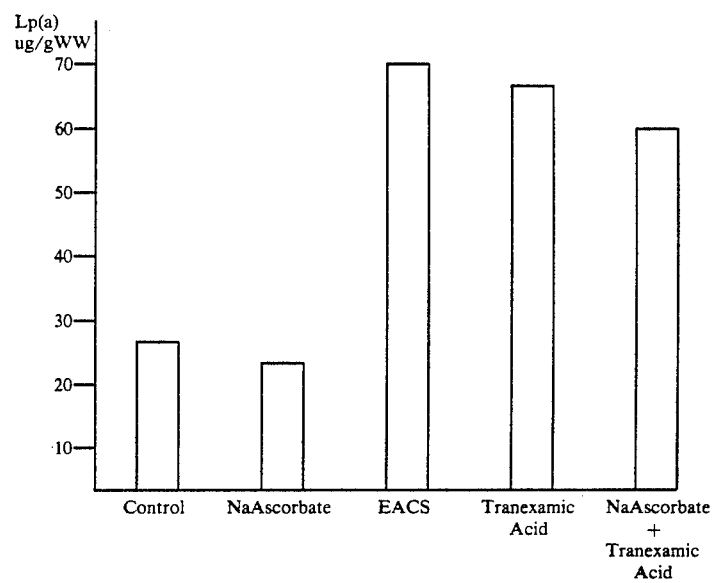

By now it is apparent that the methods and compositions of the present invention meet longstanding meeds in the field of prevention and treatment of occlusive cardiovascular disease. Although preferred embodiments and examples have been disclosed, it is understood that the invention is in no way limited by them, but rather is defined by the claims that follow and equivalents thereof.

What is claimed is:

1. A pharmaceutical composition consisting essentially of ascorbate, traexamic acid, lysine and nicotinic acid said ingredients in an amount effective to treat Lp (a)-associated occlusive cardiovascular disease.

2. A method of treatment of occlusive cardiovascular disease comprising the step of administering to a subject a therapeutic composition comprising ascorbate and tranexamic acid in an amount sufficient to decrease the binding of liproprotein (a) to blood vessel walls.

3. A method according to claim 2 wherein said ascorbate is selected from the group consisting of pharmaceutically acceptable ascorbate salts, ascorbic acid and mixtures thereof.

4. A method for treatment of occlusive cardiovascular disease comprising the step of administering to a subject a therapeutic composition comprising tranexamic acid in an amount sufficient to decrease the binding of lipoprotein(a) to blood vessel walls.

5. A method according to any one of the claims 2, 3 or 4 wherein occlusive cardiovascular disease comprises atherosclerosis and thrombosis and said vessel walls comprise arterial walls.

6. A method according to any one of the claims 2, 3 or 4 wherein said therapeutic composition is administered to a subject at risk of developing and in need of preventing for Lp (a)-associated occlusive cardiovascular disease in an amount of effective to inhibit binding of liproprotein(a) to blood vessel walls.

7. A method according to any one of the claims 2, 3 or 4 wherein said therapeutic composition is administered in an amount effective to release at least some lipoprotein(a) bound to blood vessels.

8. A method according to any one of the claims 2, 3 or 4 wherein said therapeutic composition is administered in an amount effective to reduce concentrations of lipoprotein(a) in blood serum.

9. A method for prevention of cardiovascular disease comprising the step of administering to a subject at risk of developing and in need of prevention for Lp (a)-associated occlusive cardiovascular disease a therapeutic composition comprising ascorbate and tranexamic acid in an amount sufficient to decrease binding of liproprotein(a) to blood vessel walls.

10. A method according to claim 9 wherein said ascorbate is selected from the group consisting of pharmaceutically acceptable salts of ascorbate, ascorbic acid and mixtures thereof.

11. A method of prevention of occlusive cardiovascular disease comprising the step of administering to a subject at risk of developing and in need of prevention for Lp (a)-associated occlusive cardiovascular disease a therapeutic composition comprising tranexamic acid in an amount sufficient to decrease binding of lipoprotein(a) to blood vessel walls.

12. A method according to any one of claims 9, 10 or 11 wherein said therapeutic composition is administered in an amount effective to inhibit binding of lipoprotein(a) to the blood vessel walls.

13. A method according to any one of claims 9, 10, 11, or 12 wherein said therapeutic composition is administered in an amount effective to reduce concentrations of lipoprotein(a) in blood serum.

14. A method according to any one of claims 2, 3, 4 or 9 wherein the administration is oral.

15. A method according to any one of claims 2, 3, 4 or 9 wherein administration is by parenteral application.

* * * * *